(12) United States Patent
Kim et al.

(10) Patent No.: US 8,962,900 B2
(45) Date of Patent: Feb. 24, 2015

(54) METHOD FOR PRODUCING VALUABLE AROMATICS AND LIGHT PARAFFINS FROM HYDROCARBONACEOUS OILS DERIVED FROM OIL, COAL OR WOOD

(75) Inventors: Hong Chan Kim, Jeju-si (KR); Yong Seung Kim, Seoul (KR); Sang Hun Oh, Seongnam-si (KR); Hyuck Jae Lee, Daejeon (KR); Jae Suk Koh, Daejeon (KR); Gyung Rok Kim, Daejeon (KR); Myoung Han Noh, Daejeon (KR); Sang Il Lee, Daejeon (KR); Seung Woo Lee, Daejeon (KR); Do Woan Kim, Daejeon (KR); Jae Hyun Koh, Daejeon (KR); Jong Hyung Lee, Gimpo-si (KR); Sun Choi, Daejeon (KR); Seung Hoon Oh, Seoul (KR); Kyung Jong Oh, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 178 days.

(21) Appl. No.: 13/880,838

(22) PCT Filed: Oct. 20, 2011

(86) PCT No.: PCT/KR2011/007852
§ 371 (c)(1),
(2), (4) Date: Jun. 13, 2013

(87) PCT Pub. No.: WO2012/053848
PCT Pub. Date: Apr. 26, 2012

(65) Prior Publication Data
US 2013/0267744 A1 Oct. 10, 2013

(30) Foreign Application Priority Data

Oct. 22, 2010 (KR) .................. 10-2010-0103629

(51) Int. Cl.
*C07C 5/10* (2006.01)
*C07C 5/02* (2006.01)

(52) U.S. Cl.
CPC .................................. *C07C 5/02* (2013.01)
USPC ............ 585/251; 585/253; 585/240; 585/242

(58) Field of Classification Search
CPC .......... C10G 1/00; C10G 1/002; C10G 1/006; C10G 1/06; C10G 35/00; C10G 35/04; C10G 45/44; C10G 45/48; C10G 45/50; C10G 55/00; C10G 55/06; C10G 57/005; C10G 69/00; C10G 69/12; C10G 69/123; C10G 2400/20; C10G 2400/30; C07C 5/00; C07C 5/10; C07C 5/11; C07C 5/22; C07C 15/00; C07C 15/02; C07C 15/04; C07C 15/06; C07C 15/08
USPC .................................. 585/253, 240, 242, 251
See application file for complete search history.

(56) References Cited

U.S. PATENT DOCUMENTS

| 4,585,545 A | 4/1986 | Yancey, Jr. et al. |
| 6,565,739 B2 | 5/2003 | Winter |

(Continued)

FOREIGN PATENT DOCUMENTS

| CN | 1667089 A | 9/2005 |
| CN | 101305078 A | 10/2006 |

(Continued)

OTHER PUBLICATIONS

Office Action dated May 26, 2014 for corresponding Chinese Patent Application No. 201080071134.2.
International Search Report for PCT/KR2010/008418 Dated Aug. 24, 2011.

(Continued)

*Primary Examiner* — In Suk Bullock
*Assistant Examiner* — Philip Louie
(74) *Attorney, Agent, or Firm* — Abelman, Frayne & Schwab

(57) ABSTRACT

This invention relates to a method of producing aromatics and light paraffins from hydrocarbonaceous oils derived from oil, coal or wood, including partially saturating and hydrocracking the oils derived from oil in a hydrogenation and reaction area, separating them depending on the number of carbons, recirculating heavy oils having 11 or more carbons to the hydrogenation and reaction area, feeding oils suitable for producing BTX to an aromatic separation process and a transalkylation process to recover aromatics, and feeding hydrocarbonaceous components having 5 or fewer carbons to a light separation process, thus obtaining light paraffins.

22 Claims, 1 Drawing Sheet

(56) References Cited

U.S. PATENT DOCUMENTS

| | | |
|---|---|---|
| 6,867,340 B2 | 3/2005 | Oh et al. |
| 2003/0019792 A1 | 1/2003 | Chen et al. |
| 2009/0227823 A1 | 9/2009 | Huber et al. |
| 2010/0160699 A1* | 6/2010 | Frey et al. ............... 585/316 |

FOREIGN PATENT DOCUMENTS

| | | |
|---|---|---|
| KR | 1020070051117 A | 5/2007 |
| WO | 2007/055488 A1 | 5/2007 |

OTHER PUBLICATIONS

Torren R. Carson, et al., "Aromatic Production from Catalytic Fast Pyrolysis of Biomass-Derived Feedstocks Topics in Catalysis," vol. 52, pp. 241-252 (2009).

N. Martin, et al., "Copyrolysis of wood biomass and synthetic polymers mixtures. Part II: characterization of the liquid phases," Journal of Analytical and Applied Pyrolysis, vol. 65, pp. 41-55 (2002).

International Search Report for PCT/KR2011/006813 (Mar. 26, 2012) (4 Pages).

CN2011844845.5, Office Action, Apr. 17, 2014 (10 pages).

* cited by examiner

METHOD FOR PRODUCING VALUABLE AROMATICS AND LIGHT PARAFFINS FROM HYDROCARBONACEOUS OILS DERIVED FROM OIL, COAL OR WOOD

CROSS-REFERENCE TO RELATED APPLICATIONS

This application is a National Phase of PCT/KR2011/007852, filed 20 Oct. 2011, which claims priority from Korean Application No. 10-2010-0103629, filed 22 Oct. 2010, the disclosures of which are all incorporated herein by reference.

TECHNICAL FIELD

The present invention relates to a method of producing aromatics and paraffins from hydrocarbonaceous oils derived from oil, coal or wood.

BACKGROUND ART

The demand for aromatics, for example, benzene/toluene/xylene, is increasing at a yearly average of 4~6% all over the world, which is a drastic increasing trend that is two times the GDP and three times the demand for general petroleum products. Such an increase is based on the dramatically increasing demand for aromatics in China.

Conventional aromatics (benzene/toluene/xylene) have been produced from pyrolysis gasoline obtained together with fundamental oil products including ethylene, propylene, etc., in naphtha pyrolysis plants using a naphtha feed, or from reformate in catalytic naphtha reformer.

However, because of the drastic increase in the demand for aromatics as noted above, Shortage of naphtha supply are intensifying in the worldwide market including China since 2007, conventional techniques using naphtha cannot meet the increasing aromatic demand because naphtha can be obtained by atmospheric distillation of crude oil only. Hence, there is a need for alternative feed for aromatics, which is usable as a replacement for naphtha, and furthermore, a need to increase the yield of aromatics and light paraffins is receiving attention.

DISCLOSURE OF INVENTION

Technical Problem

Under such circumstances, the present inventors have ascertained that aromatic components such as benzene, toluene or xylene, the demand for which is increasing, may be prepared from oils derived from oil, coal or wood, and therefore the present invention has been devised in response to the need by the market for the above techniques.

Accordingly, an object of the present invention is to provide a novel method of producing high-concentration aromatics using oils derived from oil, coal or wood containing a large amount of components having high aromaticity, instead of using a conventional naphtha feed for aromatics.

Solution to Problem

In order to accomplish the above object, the present invention provides a method of producing aromatics and light paraffins from oils derived from oil, coal or wood, comprising (a) introducing the oils derived from oil, coal or wood into a hydrogenation and reaction area, so that polycyclic aromatic components are partially saturated and cracked; (b) separating components obtained in (a) into hydrocarbonaceous components having 11 or more carbons, hydrocarbonaceous components having 6~10 carbons, and hydrocarbonaceous components having 5 or fewer carbons; and (c) recirculating the hydrocarbonaceous components having 11 or more carbons separated in (b) back to (a), feeding the hydrocarbonaceous components having 6~10 carbons to an aromatic separation process and a transalkylation process so that at least a portion of the aromatics is recovered, and feeding the hydrocarbonaceous components having 5 or fewer carbons to a light separation process thus obtaining aromatics and paraffins.

Advantageous Effects of Invention

A method of producing aromatics and paraffins according to the present invention enables the production of high-concentration aromatics such as benzene, toluene and xylene using oils including light cycle oil obtained by fluid catalytic cracking of oil, pyrolysis gasoline obtained by thermal cracking of naphtha, heavy aromatics from a reformer, coal tar or light oil resulting from coal carbonation, or aromatic compounds resulting from wood pyrolysis, carbonation, destructive distillation, etc., instead of using the conventional naphtha feed for aromatics, and thereby the method according to the present invention can overcome the limitations put on the throughput of aromatics.

In particular, among a variety of aromatics/paraffins, valuable aromatics, for example, benzene, toluene and xylene, and light paraffins such as propane, butane or the like can be selectively produced, and byproducts which are relatively valueless can be recovered and reprocessed so that their values are increased, thereby greatly increasing the value of the final products.

MODE FOR THE INVENTION

Hereinafter, a detailed description will be given of the present invention.

The present invention pertains to a method of producing aromatic components including benzene, toluene or xylene from oils derived from oil, coal or wood. According to the present invention, oils derived from oil may mainly include oils containing aromatic compounds such as light cycle oil (LCO), pyrolysis gasoline, heavy aromatics, etc., and oils derived from coal or wood include but are not limited to oils containing aromatic compounds such as coal tar or light oil, wood tar, etc., and all oils containing aromatic components derivable from oil, coal or wood may be used. For example, it is possible to use any materials selected from the group consisting of oils derived from oil, such as raw pyrolysis gasoline (RPG), heavy raw pyrolysis gasoline (heavy RPG), treated pyrolysis gasoline (TPG), reformate, heavy aromatics, kerosene, jet oil, atmospheric gas oil, FCC gasoline, light cracked naphtha, heavy cracked naphtha, FCC decanted oil, vacuum gas oil, coker gas oil, coker diesel, coker naphtha, heavy and reduced petroleum crude oil, petroleum atmospheric distillation bottom, petroleum vacuum distillation bottom, asphalt, bitumen, tar sand oil, shale oil, liquid/solid products obtained by coal liquefaction or coal carbonation, such as coal tar, tar oil, light oil, phenolic oil or carbolic oil, naphthalene oil, wash oil, anthracene oil, light anthracene oil, heavy anthracene oil and pitch, products derived from wood carbonation, such as wood tar, hardwood tar, resinous tar, and combinations thereof.

Figure 1:
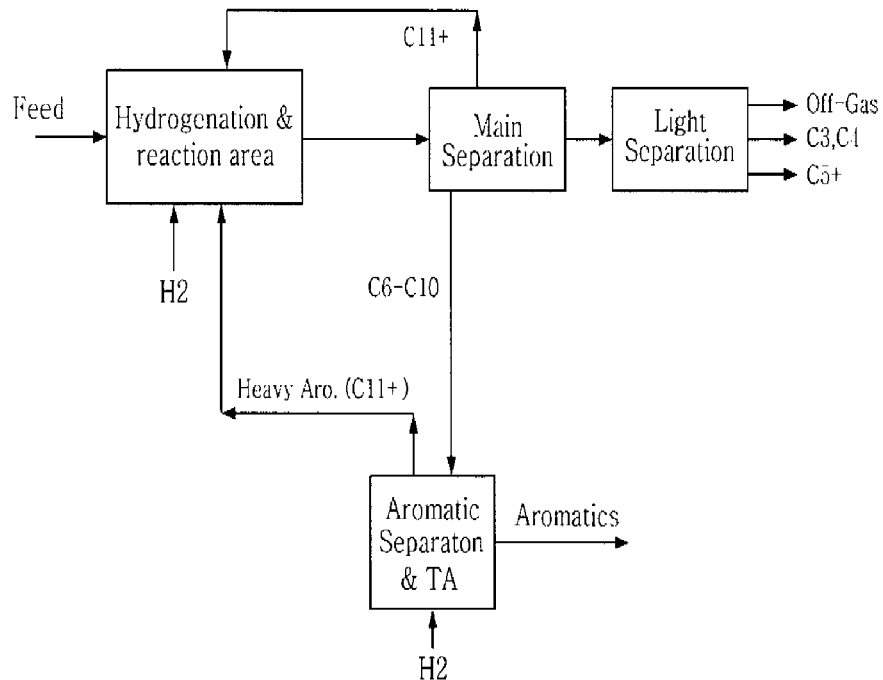
FIG. 1 is a schematic block flow diagram showing a production process according to an embodiment of the present invention.
Figure 2:
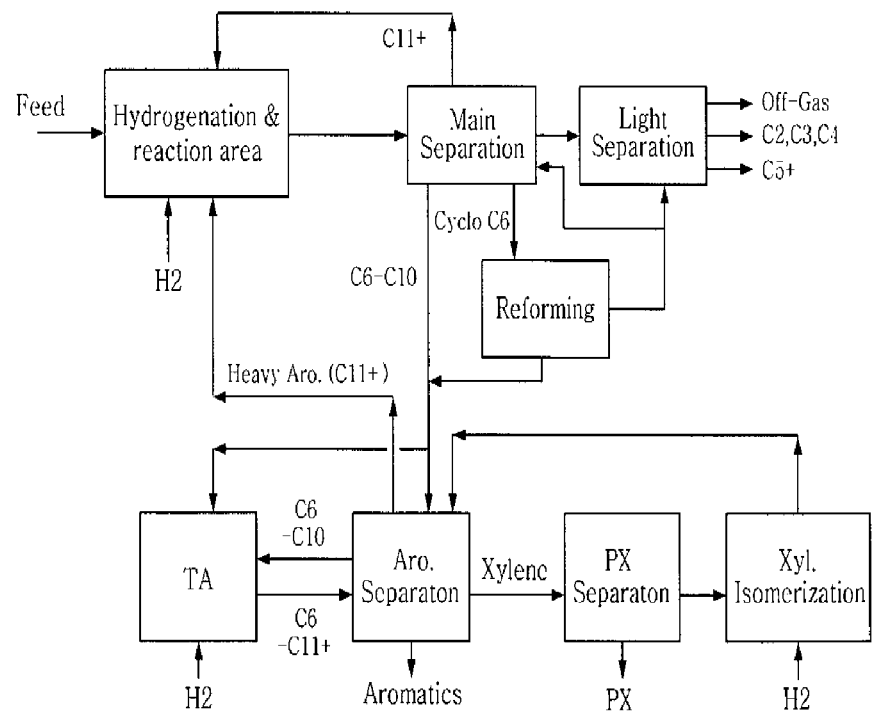
FIG. 2 is a schematic block flow diagram showing a production process according to another embodiment of the present invention, including aromatic separation, transalkylation, xylene process and then the recirculation of unconverted oils.

The schematic block flow diagram for the method according to the present invention is shown in FIG. 1. With reference to FIG. 1, the oils are introduced into a hydrogenation and reaction area. As the amount of aromatic components of the oils is increased, valuable aromatics may be favorably produced.

According to the present invention, polycyclic aromatic components may be partially saturated and cracked in the hydrogenation and reaction area. The hydrogenation and reaction area includes a hydroprocessing unit and a hydrocracking unit. As such, hydroprocessing and hydrocracking may be performed in any sequence whatsoever. Specifically, the feed may be introduced into the hydroprocessing unit and then the hydrocracking unit, or into the hydrocracking unit and then the hydroprocessing unit.

The hydroprocessing unit of the hydrogenation and reaction area is configured such that hydrogen is supplied from the outside, and the oils are hydrotreated in the presence of a hydroprocessing catalyst. The hydroprocessing reaction achieves the partial saturation of aromatic components including two or more aromatic rings. Such hydroprocessing must not saturate an aromatic component having one aromatic ring. This is because the aromatic component having one aromatic ring is a valuable aromatic component or may be converted into a valuable aromatic component by transalkylation which will be described later.

In the hydroprocessing unit, the aromatic components including two or more aromatic rings are saturated in such a manner that the aromatic rings other than only one aromatic ring are saturated. This is because it is not easy to perform the cracking of the unnecessary aromatic rings in the subsequent hydrocracking unit.

To obtain the above results, the hydroprocessing unit may operate under conditions including a reaction pressure of 20~100 kg/cm$^2$, a reaction temperature of 150~450° C., and a liquid hourly space velocity (LHSV) of 0.1~4.5 hr$^{-1}$.

Also a catalyst used in the hydrprocessing unit may comprise a carrier composed of either or both of alumina and silica, and one or more metals selected from the group consisting of metals of Groups 6, 9, and 10. Particularly useful are one or more metals selected from the group consisting of cobalt, molybdenum, nickel and tungsten.

Upon hydroprocessing, not only partial saturation of the aromatic rings but also desulfurization, denitrogenation and deoxygenation that are conducted to remove impurities such as sulfides, nitrogen or oxygen compounds from the oils may be carried out. For this process of producing aromatics, the removal of impurities is very important, and all impurities like sulfur, nitrogen and oxygen should be removed before being fed to the transalkylation process. Generally Oxygen level of oils from tar and wood is very high. Hence, the impurities in the oils may be easily removed without the need to also remove the impurities.

Upon hydroprocessing, the partially saturated feed is fed to the hydrocracking unit. A hydrocracking catalyst used in the hydrocracking unit may be composed of one or more kinds of zeolite having a pore size of 4 Å (Angstroms) or more, which may be optionally modified with a binder and one or more metals selected from among metals of Groups 6, 9 and 10. The zeolite may include but is not limited to, MOR, MEL, FAU, BEA, etc., and the binder may include silica, alumina, clay, etc., which may be used alone or in combinations thereof.

Hydrocracking plays a role in breaking a naphthenic ring or a long branch with two or more carbons attached to a 1-ring aromatic compound, in the presence of added hydrogen. As such, hydrocracking does not produce olefins, unlike catalytic cracking. According to the reaction mechanism, the cracked naphthenic ring is an unsaturated hydrocarbon (i.e. an olefin), which is unstable and thus easily binds with the other hydrocarbons around it. This reaction hinders the production of a desired aromatic component or may cause polymerization to produce coke thus undesirably deactivate the catalyst. Thus, hydrogen is added to the unsaturated hydrocarbon, which is thus converted into a saturated hydrocarbon that is stable. For this reason, hydrocracking requires a supply of hydrogen unlike catalytic cracking. The purpose of hydroprocessing is, for the aromatic components having two or more aromatic rings, partially saturating the aromatic rings other than the one aromatic ring, so that the naphthenic ring may be broken thus forming valuable aromatic components or materials that can be used to make aromatic components in subsequent procedures.

To obtain the above results, the hydrocracking unit may operate under conditions including a reaction pressure of 400~4500 psig, a reaction temperature of 200~500° C., and LHSV of 0.1~10.

The products obtained from the hydrogenation and reaction area are separated into i) hydrocarbonaceous components having 11 or more carbons, ii) hydrocarbonaceous components having 6~10 carbons and iii) hydrocarbonaceous components having 5 or fewer carbons, by means of a main separation column. The hydrocarbonaceous components having 11 or more carbons thus separated are recirculated back to the hydrogenation and reaction area, and the hydrocarbonaceous components having 6~10 carbons are fed to an aromatic separation process and a transalkylation process, and the hydrocarbonaceous components having 5 or fewer carbons are fed to a light separation process.

Heavy oils having 11 or more carbons may be converted into valuable aromatic components or valuable paraffin components, and are thus recirculated back to the hydrogenation and reaction area. Among the heavy oils obtained by the main separation column, the amount of oils passing through the hydroprocessing unit and the hydrocracking unit may vary depending on the feed but is about 40% of the total of supplied oils, and after recirculation, the amount of oils which should be further recirculated is less than just 15% of the total.

The hydrocarbonaceous components having 5 or fewer carbons that were separated by the main separation column are further separated into off-gas and paraffin components by light separation. The paraffin components include 2 or more carbons such as ethane, propane, butane, etc.

The hydrocarbonaceous components having 6~10 carbons that were separated by the main separation column are fed to the aromatic separation process and the transalkylation process. As such, among the hydrocarbonaceous components having 6~10 carbons, saturated hydrocarbons including cyclohexane are fed to an additional reformer. A portion of the oils reformed to be unsaturated using the reformer is fed to the aromatic separation process and the transalkylation process, and the unconverted oils may be fed to the main separation column or the light separation process. The reformer functions to convert the saturated hydrocarbons into aromatic components at about 400~600° C. using a Pt/$Al_2O_3$, Pt—Re/$Al_2O_3$ or Pt—Sn/$Al_2O_3$ catalyst in a hydrogen atmosphere. The products obtained by the reformer may include benzene, toluene and xylene, and such unsaturated hydrocarbons are fed to the aromatic separation process and the transalkylation process.

The hydrocarbonaceous components having 6~10 carbons separated by the main separation column (and the reformer) are transferred to the aromatic separation process and the transalkylation process. As such, aromatic separation and transalkylation may be performed in any sequence whatsoever. Specifically, (i) the hydrocarbonaceous components having 6~10 carbons may be separated into benzene, toluene, xylene, and hydrocarbonaceous components having 9 or more carbons in the aromatic separation process, after which a portion of the separated oils is transferred to the transalkylation process, thus obtaining a mixture comprising benzene, toluene, xylene, and hydrocarbonaceous components having 9 or more carbons, after which this mixture is further mixed with the remainder of the oils that were not transferred to the transalkylation process, followed by feeding the resulting mixture to the aromatic separation process, thereby recovering the desired aromatics, or (ii) the hydrocarbonaceous components having 6~10 carbons may be directly transferred to the transalkylation process, thus obtaining a mixture comprising benzene, toluene, xylene, and hydrocarbonaceous components having 9 or more carbons, after which this mixture may be fed to the aromatic separation process, thus recovering the desired aromatics.

Upon the transalkylation, dealkylation of alkylaromatic compounds having 9 or more carbons and the transalkylation between benzene and aromatic compounds having 9 or more carbons occur simultaneously along with disproportionation of toluene in the presence of a catalyst and transalkylation between toluene and aromatic compounds having 9 or more carbons.

Such dealkylation is an important reaction that produces toluene necessary for disproportionation and transalkylation. Also, transalkylation between benzene and aromatic compounds having 9 or more carbons is regarded as important because it produces toluene and xylene.

On the other hand, olefins including ethylene, propylene, etc., produced by dealkylation, have to be rapidly hydrogenated. Unless such olefins are rapidly hydrogenated, they are re-alkylated to aromatic compounds, ultimately lowering the rate of conversion of aromatic compounds having 9 or more carbons. Furthermore, olefins themselves may cause polymerization or the like, undesirably facilitating the production of coke that deactivates the catalyst.

The catalyst used for transalkylation is not limited, but may include a catalyst disclosed in U.S. Pat. No. 6,867,340 by the present applicant.

Specifically transalkylation is performed using a catalyst comprising a carrier composed of 10~95 wt % of beta-zeolite or mordenite having a molar ratio of silica/alumina adjusted to 20~200 based on alumina and 5~90 wt % of one or more inorganic binders selected from the group consisting of gamma-alumina, silica, silica alumina, bentonite, kaolin, clinoptilolite and montmorillonite, and a hydrogenation metal composed of, based on 100 parts by weight of the carrier, 0.001~0.5 parts by weight of one or more metals selected from the group consisting of platinum, tin, indium and lead. The other properties of the catalyst are to be found in the above literature.

After transalkylation, the aromatic components having 11 or more carbons, which are not used as materials to make valuable aromatic components, are recovered, and then may be fed to the hydrogenation and reaction area. Also, benzene, toluene, xylene and hydrocarbons having 9 or more carbons produced by transalkylation may be fed to a xylene process which will be described later via the aromatic separation process. In the xylene process, separating para-xylene from xylene mixture (composed of ortho-xylene, meta-xylene and para-xylene) and isomerizing the xylene mixture other than para-xylene into para-xylene may be performed.

Also, para-xylene (p-X) separation for separating only para-xylene from xylene mixture may be performed using a technique known in the art, such as adsorption, crystallization, etc.

Because para-xylene is much more valuable than ortho-xylene or meta-xylene, the separation and recovery of only para-xylene is favorable.

The xylene components including ortho-xylene and meta-xylene, except for para-xylene, may be transferred to the xylene isomerization process. Among the xylene mixture produced by aromatic separation, para-xylene, meta-xylene, and ortho-xylene are in a state of equilibrium. Because only para-xylene is separated by the above separation, the xylene mixture other than para-xylene are equilibrated using a catalyst, whereby para-xylene which is economically valuable may be additionally obtained.

On the other hand, the method according to the present invention may include recovering at least a portion of aromatics, for example, benzene and xylene mixture, from among aromatics resulting from transalkylation and xylene process, and recirculating the unconverted oils. Specifically, a portion of benzene and toluene among aromatics resulting from transalkylation may be recirculated back to the aromatic separation process and may thus be further fed to the transalkylation process, and also may be recirculated back to the hydrogenation and reaction area from the aromatic separation process. Moreover, in the xylene isomerization process, oils which were not isomerized into para-xylene may be recirculated back to the aromatic separation process, and thus may be fed to the transalkylation process or the xylene process.

Accordingly, all of the oils obtained from the xylene isomerization process may be recirculated back to the transalkylation process and the para-xylene separation process via the aromatic separation process, thus additionally obtaining para-xylene.

Specifically, the recirculation procedure from the transalkylation process and the xylene isomerization process to the aromatic separation process may increase the yield of para-xylene, and improvements in the yield of paraffins and valuable aromatics are possible without performing additional treatment and without wasting any materials thanks to the recirculation from the aromatic separation process to the hydrogenation and reaction area.

According to embodiments of the present invention, as a feed, LCO derived from oil or coal tar derived from coal is introduced into the hydrogenation and reaction area that performs hydroprocessing and hydrocracking. The oils cracked in the hydrogenation and reaction area are fed to the main separation column so that they are separated into (i) components having 6~10 carbons, (ii) light paraffin components, and (iii) hydrocarbonaceous components having 11 or more carbons.

After being separated by the main separation column, (iii) the oils having 11 or more carbons are mixed with the above feed and then recirculated back to the hydrogenation and reaction area.

By such recirculation, aromatic components having two or more rings may be cracked to a 1-ring aromatic component using hydroprocessing and hydrocracking catalysts, and hydrocarbonaceous groups having two or more carbons or naphthenic rings may also be cracked and converted into valuable aromatic components or materials to make valuable aromatic components.

When the recirculation is performed in this way, the amount of aromatic components having two or more rings may be drastically reduced, compared to when recirculation is not performed. Furthermore, the amount thereof which is converted into valuable aromatics or materials to make valuable aromatics may be considerably increased.

Also, because the composition of (i) the components having 6~10 carbons varies depending on the feed used in examples, the aromatic separation process, the transalkylation process, and the xylene process may be differently configured to suit the properties of the components, and the unconverted oils are recirculated to the hydrogenation and reaction area.

When the configuration of these process is changed and the recirculation is additionally used as mentioned above, unnecessary components are prevented from accumulating upon transalkylation and xylene process, and the components which are not used as materials to make valuable aromatic components may be converted into valuable aromatic components, thus increasing the yield of valuable aromatics. The recirculation effects are described in detail in the following Examples 1 and 2.

In order to additionally explain the principle of the present invention, the examples are described below, but the present examples are not supposed to limit the scope of the present invention as envisioned by the present inventors.

EXAMPLE

Example 1

Production of Valuable Aromatics and Light Paraffins from LCO

Production of Valuable Aromatics and Light Paraffins from LCO Using Hydrogenation Reaction, Aromatic Separation, and Transalkylation LCO used in this example was composed of cracked oils resulting from fluid catalytic cracking (FCC). The properties, compositions and yield of the oils resulting from FCC may differ depending on the feed and operating conditions in an FCC unit. In the present example, LCO having a boiling point of 170~360° C. among the oils resulting from FCC was prepared as shown in Table 1 below.

TABLE 1

| Composition | Feed Amount |
|---|---|
| Paraffin | 4.68 |
| Ethane | 0.00 |
| Propane | 0.00 |
| Butane | 0.00 |
| Naphthene | 0.50 |
| Total of Aromatics | 84.12 |
| Total of 1-ring Aromatics | 39.02 |
| 1-ring Aromatic without naphthenic ring | 26.95 |
| B | 0.02 |
| T | 0.34 |
| X | 1.72 |
| C9 | 7.61 |
| C10 | 11.55 |
| 1-ring Aromatic with one naphthenic ring | 12.07 |
| 1-ring Aromatic with two naphthenic rings | 0.00 |
| Total of 2-ring Aromatics | 40.98 |
| 2-ring Aromatic without naphthenic ring | 38.40 |

TABLE 1-continued

| Composition | Feed Amount |
|---|---|
| 2-ring Aromatic with one naphthenic ring | 2.58 |
| 2-ring Aromatic with two naphthenic rings | 0.00 |
| Total of 3-ring Aromatics | 4.12 |
| Others | 10.70 |

The above feed was introduced into a hydroprocessing unit. Hydroprocessing was performed in a fixed-bed reactor in the presence of a nickel-molybdenum combined catalyst. The hydroprocessing reaction conditions are shown in Table 2 below.

TABLE 2

| Catalyst | NiMo/Al$_2$O$_3$ |
|---|---|
| Operating Conditions | |
| Reaction Pressure, kg/ | 60 |
| LHSV, hr$^{-1}$ | 1.5 |
| Reaction Temperature, ° C. | 300 |

After hydroprocessing, the composition was changed as shown in Table 3 below.

TABLE 3

| Composition | Feed Amount | After Hydroprocessing |
|---|---|---|
| Paraffin | 4.68 | 5.38 |
| Ethane | 0.00 | 0.01 |
| Propane | 0.00 | 0.01 |
| Butane | 0.00 | 0.01 |
| Naphthene | 0.50 | 1.74 |
| Total of Aromatics | 84.12 | 80.02 |
| Total of 1-ring Aromatics | 39.02 | 71.33 |
| 1-ring Aromatic without naphthenic ring | 26.95 | 27.28 |
| B | 0.02 | 0.00 |
| T | 0.34 | 0.10 |
| X | 1.72 | 0.84 |
| C9 | 7.61 | 5.08 |
| C10 | 11.55 | 10.39 |
| 1-ring Aromatic with one naphthenic ring | 12.07 | 39.89 |
| 1-ring Aromatic with two naphthenic rings | 0.00 | 4.16 |
| Total of 2-ring Aromatics | 40.98 | 8.03 |
| 2-ring Aromatic without naphthenic ring | 38.40 | 4.29 |
| 2-ring Aromatic with one naphthenic ring | 2.58 | 3.60 |
| 2-ring Aromatic with two naphthenic rings | 0.00 | 0.13 |
| Total of 3-ring Aromatics | 4.12 | 0.66 |
| Others | 10.70 | 13.63 |

As is apparent from Table 3, before hydroprocessing, the amount of the components including two or more aromatic rings was considerable but was drastically reduced after hydroprocessing. Also the amount of the 1-ring aromatic component was increased about 80%, and in particular, the amount of the 1-ring aromatic component having the naphthenic ring was increased from about 12.07 to about 39.89, namely at least 230%, based on a value of 100 for the feed. The 1-ring aromatic component having the naphthenic ring may be formed into a valuable aromatic component or a direct material to make the valuable aromatic component by breaking the naphthenic ring in the hydrocracking unit.

The products obtained from the hydroprocessing unit were supplied to a hydrocracking reactor, so that hydrocracking was carried out. The catalyst used herein was a combination of cobalt and beta-zeolite, and the reaction temperature was 380° C., and the reaction pressure was 1200 psig.

After hydrocracking, the composition was changed as shown in Table 4 below.

TABLE 4

| Composition | Feed Amount | After Hydroprocessing | After Hydrocracking |
|---|---|---|---|
| Paraffin | 4.68 | 5.38 | 40.85 |
| Ethane | 0.00 | 0.01 | 0.41 |
| Propane | 0.00 | 0.01 | 8.20 |
| Butane | 0.00 | 0.01 | 19.25 |
| Naphthene | 0.50 | 1.74 | 1.51 |
| Total of Aromatics | 84.12 | 80.02 | 59.98 |
| Total of 1-ring Aromatics | 39.02 | 71.33 | 55.52 |
| 1-ring Aromatic without naphthenic ring | 26.95 | 27.28 | 52.72 |
| B | 0.02 | 0.00 | 1.79 |
| T | 0.34 | 0.10 | 9.04 |
| X | 1.72 | 0.84 | 16.44 |
| C9 | 7.61 | 5.08 | 15.14 |
| C10 | 11.55 | 10.39 | 8.34 |
| 1-ring Aromatic with one naphthenic ring | 12.07 | 39.89 | 2.50 |
| 1-ring Aromatic with two naphthenic rings | 0.00 | 4.16 | 0.30 |
| Total of 2-ring Aromatics | 40.98 | 8.03 | 4.41 |
| 2-ring Aromatic without naphthenic ring | 38.40 | 4.29 | 2.57 |
| 2-ring Aromatic with one naphthenic ring | 2.58 | 3.60 | 1.84 |
| 2-ring Aromatic with two naphthenic rings | 0.00 | 0.13 | 0.00 |
| Total of 3-ring Aromatics | 4.12 | 0.66 | 0.06 |
| Others | 10.70 | 13.63 | 1.99 |

As is apparent from Table 4, compared to the feed before hydrocracking, namely, the feed after hydroprocessing, the amount of benzene and xylene which are valuable aromatic components was increased by 2000% or more. Also, the amount of toluene/C9/C10 which are the materials used to make the benzene/xylene by subsequent transalkylation was increased by about 109%. Upon hydrocracking, only paraffin, not olefin, was produced.

Among the components produced by hydrocracking, light paraffins were recovered, and components having 6~10 carbons were fed to the transalkylation process. The catalyst used in the transalkylation process was composed of a carrier comprising 50 wt % of mordenite having a molar ratio of silica/alumina of 90 and 50 wt % of gamma-alumina binder and 0.05 parts by weight of platinum and 0.5 parts by weight of tin supported thereon. The composition of the products obtained by transalkylation is shown in Table 5 below.

TABLE 5

| Composition | Feed Amount | After Hydroprocessing | After Hydrocracking | After Transalkylation |
|---|---|---|---|---|
| Paraffin | 4.68 | 5.38 | 40.85 | 49.18 |
| Ethane | 0.00 | 0.01 | 0.41 | 5.08 |
| Propane | 0.00 | 0.01 | 8.20 | 10.95 |
| Butane | 0.00 | 0.01 | 19.25 | 20.18 |
| Naphthene | 0.50 | 1.74 | 1.51 | 0.02 |
| Total of Aromatics | 84.12 | 80.02 | 59.98 | 53.76 |
| Total of 1-ring Aromatics | 39.02 | 71.33 | 55.52 | 49.30 |
| 1-ring Aromatic without naphthenic ring | 26.95 | 27.28 | 52.72 | 47.26 |
| B | 0.02 | 0.00 | 1.79 | 7.95 |
| T | 0.34 | 0.10 | 9.04 | 0.00 |
| X | 1.72 | 0.84 | 16.44 | 34.89 |
| C9 | 7.61 | 5.08 | 15.14 | 0.00 |
| C10 | 11.55 | 10.39 | 8.34 | 2.83 |
| 1-ring Aromatic with one naphthenic ring | 12.07 | 39.89 | 2.50 | 1.74 |
| 1-ring Aromatic with two naphthenic rings | 0.00 | 4.16 | 0.30 | 0.30 |
| Total of 2-ring Aromatics | 40.98 | 8.03 | 4.41 | 4.41 |
| 2-ring Aromatic without naphthenic ring | 38.40 | 4.29 | 2.57 | 2.57 |
| 2-ring Aromatic with one naphthenic ring | 2.58 | 3.60 | 1.84 | 1.84 |
| 2-ring Aromatic with two naphthenic rings | 0.00 | 0.13 | 0.00 | 0.00 |
| Total of 3-ring Aromatics | 4.12 | 0.66 | 0.06 | 0.06 |
| Others | 10.70 | 13.63 | 1.99 | 1.99 |

As is apparent from Table 5, compared to the feed before transalkylation, the feed after transalkylation had benzene as the valuable aromatic component, the amount of which was increased by 345%, and xylene which further increased in amount by 112%. Because the transalkylation was not a cracking procedure, there was a additional increase in the amount of light parraffins not olefins.

Production of Valuable Aromatics and Light Paraffins from LCO by Recirculation of Hydrocarbons Having 11 or More Carbons In the process of producing valuable aromatics, the same feed and reaction conditions were applied, with the exception that the hydrocarbonaceous components having 11 or more carbons resulting from hydroprocessing and hydrocracking were recirculated back to the hydrogenation and reaction area.

The LCO feed (A0), the product (A1) obtained without recirculating hydrocarbons having 11 or more carbons, and the product (A2) obtained by recirculating hydrocarbons having 11 or more carbons are shown in Table 6 below.

TABLE 6

| Composition | A0 | A1 | A2 |
|---|---|---|---|
| Paraffin | 4.68 | 49.18 | 55.98 |
| Ethane | 0.00 | 5.08 | 5.78 |
| Propane | 0.00 | 10.95 | 12.47 |
| Butane | 0.00 | 20.18 | 22.97 |
| Naphthene | 0.50 | 0.02 | 0.02 |
| Total of Aromatics | 84.12 | 53.76 | 49.69 |
| Total of 1-ring Aromatics | 39.02 | 49.30 | 49.69 |
| 1-ring Aromatic without naphthenic ring | 26.95 | 47.26 | 49.69 |
| B | 0.02 | 7.95 | 9.05 |
| T | 0.34 | 0.00 | 0.00 |
| X | 1.72 | 34.89 | 39.72 |
| C9 | 7.61 | 0.00 | 0.00 |
| C10 | 11.55 | 2.83 | 0.91 |
| 1-ring Aromatic with one naphthenic ring | 12.07 | 1.74 | 0.00 |
| 1-ring Aromatic with two naphthenic rings | 0.00 | 0.30 | 0.00 |
| Total of 2-ring Aromatics | 40.98 | 4.41 | 0.00 |
| 2-ring Aromatic without naphthenic ring | 38.40 | 2.57 | 0.00 |
| 2-ring Aromatic with one naphthenic ring | 2.58 | 1.84 | 0.00 |
| 2-ring Aromatic with two naphthenic rings | 0.00 | 0.00 | 0.00 |
| Total of 3-ring Aromatics | 4.12 | 0.06 | 0.00 |
| Others | 10.70 | 1.99 | 0.00 |

As is apparent from Table 6, recirculation was additionally performed, whereby the aromatic components having two or more rings were excluded and as the valuable aromatic components, benzene was increased by 14% and xylene was further increased by 14%. The total of light paraffins was increased by about 14%. Therefore, higher yields of the valuable aromatics and light paraffins could be obtained because of recirculation.

Production of Valuable Aromatics and Light Paraffins from LCO by Recirculation of Unconverted Oils after Transalkylation In the process of producing valuable aromatics by recirculating the hydrocarbonaceous components having 11 or more carbons to the hydroprocessing unit, the same feed and reaction conditions were applied, with the exception that, among valuable aromatic components resulting from transalkylation, a portion of benzene, toluene and xylene was recovered via the aromatic separation process, and the remainder thereof was repetitively recirculated back to the transalkylation process and the hydrogenation and reaction area.

The LCO feed (A0), the product (A1) obtained without recirculating hydrocarbons having 11 or more carbons, the product (A2) obtained by recirculating hydrocarbons having 11 or more carbons, and the product (A3) obtained by recirculating unconverted heavy oils after transalkylation are shown in Table 7 below.

TABLE 7

| Composition | A0 | A1 | A2 | A3 |
|---|---|---|---|---|
| Paraffin | 4.68 | 49.18 | 55.98 | 56.50 |
| Ethane | 0.00 | 5.08 | 5.78 | 5.83 |
| Propane | 0.00 | 10.95 | 12.47 | 12.51 |
| Butane | 0.00 | 20.18 | 22.97 | 23.02 |
| Naphthene | 0.50 | 0.02 | 0.02 | 0.02 |
| Total of Aromatics | 84.12 | 53.76 | 49.69 | 49.17 |
| Total of 1-ring Aromatics | 39.02 | 49.30 | 49.69 | 49.17 |
| 1-ring Aromatic without naphthenic ring | 26.95 | 47.26 | 49.69 | 49.17 |
| B | 0.02 | 7.95 | 9.05 | 9.14 |
| T | 0.34 | 0.00 | 0.00 | 0.00 |
| X | 1.72 | 34.89 | 39.72 | 40.02 |
| C9 | 7.61 | 0.00 | 0.00 | 0.00 |
| C10 | 11.55 | 2.83 | 0.91 | 0.00 |
| 1-ring Aromatic with one naphthenic ring | 12.07 | 1.74 | 0.00 | 0.00 |
| 1-ring Aromatic with two naphthenic rings | 0.00 | 0.30 | 0.00 | 0.00 |
| Total of 2-ring Aromatics | 40.98 | 4.41 | 0.00 | 0.00 |
| 2-ring Aromatic without naphthenic ring | 38.40 | 2.57 | 0.00 | 0.00 |
| 2-ring Aromatic with one naphthenic ring | 2.58 | 1.84 | 0.00 | 0.00 |
| 2-ring Aromatic with two naphthenic rings | 0.00 | 0.00 | 0.00 | 0.00 |
| Total of 3-ring Aromatics | 4.12 | 0.06 | 0.00 | 0.00 |
| Others | 10.70 | 1.99 | 0.00 | 0.00 |

As is apparent from Table 7, recirculation was carried out two times, whereby the amount of benzene and xylene which are valuable aromatic components was increased by 0.4 wt %, and the amount of light paraffins such as ethane, propane and butane was increased by 0.14 w %, compared to when recirculation was performed one time. Therefore, higher yields of the valuable aromatics could be obtained by carrying out recirculation two times.

Production of Valuable Aromatics and Light Paraffins from LCO by Xylene Process after Transalkylation In the recirculation of unconverted oils after transalkylation, the same feed and reaction conditions were applied, with the exception that the xylene mixture obtained by transalkylation were treated with Xylene Process comprising paraxylene separation and xylene isomerization.

The LCO feed (A0), the product (A1) obtained without recirculating hydrocarbons having 11 or more carbons, the product (A2) obtained by recirculating hydrocarbons having 11 or more carbons, the product (A3) obtained by recirculating unconverted heavy oils after transalkylation, and the product (A4) obtained by xylene isomerization and separation are shown in Table 8 below.

TABLE 8

| Composition | A0 | A1 | A2 | A3 | A4 |
|---|---|---|---|---|---|
| Paraffin | 4.68 | 49.18 | 55.98 | 56.50 | 57.02 |
| Ethane | 0.00 | 5.08 | 5.78 | 5.83 | 6.10 |
| Propane | 0.00 | 10.95 | 12.47 | 12.51 | 12.63 |
| Butane | 0.00 | 20.18 | 22.97 | 23.02 | 23.02 |
| Naphthene | 0.50 | 0.02 | 0.02 | 0.02 | 0.02 |
| Total of Aromatics | 84.12 | 53.76 | 49.69 | 49.17 | 48.66 |
| Total of 1-ring Aromatics | 39.02 | 49.30 | 49.69 | 49.17 | 48.66 |
| 1-ring Aromatic without naphthenic ring | 26.95 | 47.26 | 49.69 | 49.17 | 48.66 |
| B | 0.02 | 7.95 | 9.05 | 9.14 | 9.86 |
| T | 0.34 | 0.00 | 0.00 | 0.00 | 0.00 |
| Mixed-X | 1.45 | 34.07 | 39.72 | 39.04 | 38.80 (*) |
| EB | 0.27 | 0.82 | 0.94 | 0.98 | 0.00 |
| C9 | 7.61 | 0.00 | 0.00 | 0.00 | 0.00 |
| C10 | 11.55 | 2.83 | 0.91 | 0.00 | 0.00 |
| 1-ring Aromatic with one naphthenic ring | 12.07 | 1.74 | 0.00 | 0.00 | 0.00 |
| 1-ring Aromatic with two naphthenic rings | 0.00 | 0.30 | 0.00 | 0.00 | 0.00 |
| Total of 2-ring Aromatics | 40.98 | 4.41 | 0.00 | 0.00 | 0.00 |
| 2-ring Aromatic without naphthenic ring | 38.40 | 2.57 | 0.00 | 0.00 | 0.00 |
| 2-ring Aromatic with one naphthenic ring | 2.58 | 1.84 | 0.00 | 0.00 | 0.00 |
| 2-ring Aromatic with two naphthenic rings | 0.00 | 0.00 | 0.00 | 0.00 | 0.00 |
| Total of 3-ring Aromatics | 4.12 | 0.06 | 0.00 | 0.00 | 0.00 |
| Others | 10.70 | 1.99 | 0.00 | 0.00 | 0.00 |

(*) Para-Xylene

As is apparent from Table 8, almost of the xylene mixture could be converted into para-xylene which is a valuable product by para-xylene separation and xylene isomerization, and ethylbenzene (EB) which is an impurity in the xylene component was completely removed and converted into benzene. Therefore, the yield and purity of valuable aromatic, Paraxylene could be increased by additionally carrying out xylene process.

Example 2

Production of Valuable Aromatics and Light Paraffins from Coal Tar

Production of Valuable Aromatics and Light Paraffins from Coal Tar Using Hydroprocessing and Hydrocracking Reaction, Aromatic Separation, and Transalkylation The properties and compositions of oils derived from coal used in this example may differ depending on the feed and operating conditions. In the present example, as oils resulting from coal carbonation, coal tar having a boiling point of 78~350° C. and having the composition shown in Table 9 below was prepared.

TABLE 9

| Composition | Feed Amount |
|---|---|
| Paraffin | 0.77 |
| Ethane | 0.00 |
| Propane | 0.77 |
| Butane | 0.00 |
| Naphthene | 0.00 |
| Total of Aromatics | 99.23 |
| Total of 1-ring Aromatics | 9.73 |
| 1-ring Aromatic without naphthenic ring | 6.30 |
| B | 2.05 |
| T | 0.70 |
| X | 1.59 |
| C9 | 1.65 |
| C10 | 0.30 |

TABLE 9-continued

| Composition | Feed Amount |
| --- | --- |
| 1-ring Aromatic with one naphthenic ring | 3.43 |
| 1-ring Aromatic with two naphthenic rings | 0.00 |
| Total of 2-ring Aromatics | 89.50 |
| 2-ring Aromatic without naphthenic ring | 66.92 |
| 2-ring Aromatic with one naphthenic ring | 22.58 |
| 2-ring Aromatic with two naphthenic rings | 0.00 |
| Total of 3-ring Aromatics | 0.00 |
| Others | 0.00 |

The coal tar having the above composition was introduced into a hydroprocessing unit. Hydroprocessing was performed in a fixed-bed reactor using a nickel-molybdenum combined catalyst. The hydroprocessing reaction conditions are shown in Table 10 below.

TABLE 10

| Catalyst | NiMo/Al$_2$O$_3$ |
| --- | --- |
| Operating Conditions | |
| Reaction Pressure, kg/ | 60 |
| LHSV, hr$^{-1}$ | 1.5 |
| Reaction Temperature, °C. | 300 |

After hydroprocessing, the composition was changed as shown in Table 11 below.

TABLE 11

| Composition | Feed Amount | After Hydroprocessing |
| --- | --- | --- |
| Paraffin | 0.77 | 0.81 |
| Ethane | 0.00 | 0.00 |
| Propane | 0.77 | 0.81 |
| Butane | 0.00 | 0.00 |
| Naphthene | 0.00 | 0.00 |
| Total of Aromatics | 99.23 | 104.47 |
| Total of 1-ring Aromatics | 9.73 | 83.73 |
| 1-ring Aromatic without naphthenic ring | 6.30 | 6.63 |
| B | 2.05 | 2.16 |
| T | 0.70 | 0.74 |
| X | 1.59 | 1.68 |
| C9 | 1.65 | 1.73 |
| C10 | 0.30 | 0.32 |
| 1-ring Aromatic with one naphthenic ring | 3.43 | 61.59 |
| 1-ring Aromatic with two naphthenic rings | 0.00 | 15.51 |
| Total of 2-ring Aromatics | 89.50 | 20.74 |
| 2-ring Aromatic without naphthenic ring | 66.92 | 12.48 |
| 2-ring Aromatic with one naphthenic ring | 22.58 | 8.26 |
| 2-ring Aromatic with two naphthenic rings | 0.00 | 0.00 |
| Total of 3-ring Aromatics | 0.00 | 0.00 |
| Others | 0.00 | 0.00 |

As is apparent from Table 11, before hydroprocessing, the amount of the components including two or more aromatic rings was considerable but was drastically reduced after hydroprocessing. Also the amount of the 1-ring aromatic component was increased about 7.6 times or more, and in particular, the amount of the 1-ring aromatic component having the naphthenic ring was increased from about 3.43 to about 61.59, namely 17 times, based on a value of 100 for the feed. The 1-ring aromatic component having the naphthenic ring may be formed into a valuable aromatic component or a direct material to make the valuable aromatic component by breaking the naphthenic ring in the hydrocracking unit.

The products obtained from the hydroprocessing unit were supplied to a hydrocracking reactor, so that hydrocracking was carried out. The catalyst used herein was a combination of cobalt and beta-zeolite, and the reaction temperature was 370° C., and the reaction pressure was 1100 psig.

After the cracking, the composition was changed as shown in Table 12 below.

TABLE 12

| Composition | Feed Amount | After Hydroprocessing | After Hydrocracking |
| --- | --- | --- | --- |
| Paraffin | 0.77 | 0.81 | 35.63 |
| Ethane | 0.00 | 0.00 | 0.30 |
| Propane | 0.77 | 0.81 | 9.80 |
| Butane | 0.00 | 0.00 | 14.51 |
| Naphthene | 0.00 | 0.00 | 0.90 |
| Total of Aromatics | 99.23 | 104.47 | 70.70 |
| Total of 1-ring Aromatics | 9.73 | 83.73 | 50.39 |
| 1-ring Aromatic without naphthenic ring | 6.30 | 6.63 | 47.72 |
| B | 2.05 | 2.16 | 19.95 |
| T | 0.70 | 0.74 | 9.36 |
| X | 1.59 | 1.68 | 9.58 |
| C9 | 1.65 | 1.73 | 5.51 |
| C10 | 0.30 | 0.32 | 2.99 |
| 1-ring Aromatic with one naphthenic ring | 3.43 | 61.59 | 2.67 |
| 1-ring Aromatic with two naphthenic rings | 0.00 | 15.51 | 0.00 |
| Total of 2-ring Aromatics | 89.50 | 20.74 | 20.29 |
| 2-ring Aromatic without naphthenic ring | 66.92 | 12.48 | 20.27 |
| 2-ring Aromatic with one naphthenic ring | 22.58 | 8.26 | 0.02 |
| 2-ring Aromatic with two naphthenic rings | 0.00 | 0.00 | 0.00 |
| Total of 3-ring Aromatics | 0.00 | 0.00 | 0.02 |
| Others | 0.00 | 0.00 | 0.56 |

As is apparent from Table 12, compared to the feed before the cracking, namely, the feed after hydroprocessing, the amount of benzene and xylene which are valuable aromatic components was increased by about 670% or more. Also, the amount of toluene/C9/C10, which are the materials used to make the benzene/xylene by subsequent transalkylation, was increased by about 540%. In the hydrocracking unit, only paraffins, not olefins, were produced.

Among the components produced by hydrocracking, the light paraffins were recovered, and components having 6~10 carbons were fed to the aromatic separation process, so that benzene was separated and the remaining components were fed to the transalkylation process. In Example 1, because the amount of the benzene component is not large, even when the components having 6~10 carbons are directly fed to the transalkylation process without separation of benzene, a load on the transalkylation process is small and the process is simplified. However, in the present example, because the amount of the benzene component is large, when the components having 6~10 carbons are fed to the transalkylation process without the separation of benzene, the load on the transalkylation process is large, undesirably increasing the investment cost and comparatively decreasing the yield of valuable aromatics.

The catalyst used upon transalkylation was composed of a carrier comprising 50 wt % of mordenite having a molar ratio of silica/alumina of 90 and 50 wt % of gamma-alumina binder and 0.05 parts by weight of platinum and 0.5 parts by weight of tin supported thereon. The composition of the products obtained by transalkylation is shown in Table 13 below.

TABLE 13

| Composition | Feed Amount | After Hydro-processing | After Hydro-cracking | After Trans-alkylation |
| --- | --- | --- | --- | --- |
| Paraffin | 0.77 | 0.81 | 35.63 | 40.82 |
| Ethane | 0.00 | 0.00 | 0.30 | 3.07 |

TABLE 13-continued

| Composition | Feed Amount | After Hydro-processing | After Hydro-cracking | After Trans-alkylation |
|---|---|---|---|---|
| Propane | 0.77 | 0.81 | 9.80 | 11.43 |
| Butane | 0.00 | 0.00 | 14.51 | 15.06 |
| Naphthene | 0.00 | 0.00 | 0.90 | 0.01 |
| Total of Aromatics | 99.23 | 104.47 | 70.70 | 66.77 |
| Total of 1-ring Aromatics | 9.73 | 83.73 | 50.39 | 46.46 |
| 1-ring Aromatic without naphthenic ring | 6.30 | 6.63 | 47.72 | 44.82 |
| B | 2.05 | 2.16 | 19.95 | 28.20 |
| T | 0.70 | 0.74 | 9.36 | 0.00 |
| X | 1.59 | 1.68 | 9.58 | 15.01 |
| C9 | 1.65 | 1.73 | 5.51 | 0.00 |
| C10 | 0.30 | 0.32 | 2.99 | 1.33 |
| 1-ring Aromatic with one naphthenic ring | 3.43 | 61.59 | 2.67 | 1.64 |
| 1-ring Aromatic with two naphthenic rings | 0.00 | 15.51 | 0.00 | 0.00 |
| Total of 2-ring Aromatics | 89.50 | 20.74 | 20.29 | 20.29 |
| 2-ring Aromatic without naphthenic ring | 66.92 | 12.48 | 20.27 | 20.27 |
| 2-ring Aromatic with one naphthenic ring | 22.58 | 8.26 | 0.02 | 0.02 |
| 2-ring Aromatic with two naphthenic rings | 0.00 | 0.00 | 0.00 | 0.00 |
| Total of 3-ring Aromatics | 0.00 | 0.00 | 0.02 | 0.02 |
| Others | 0.00 | 0.00 | 0.56 | 0.56 |

As is apparent from Table 13, compared to the feed before transalkylation, the feed after transalkylation had benzene as the valuable aromatic component, the amount of which was increased by 41%, and xylene which further increased in amount by 57%. Because the transalkylation was not a cracking procedure, there was a additional increase in the amount of light paraffins not olefins.

Production of Valuable Aromatics and Light Paraffins from Coal Tar by Recirculation of Hydrocarbons Having 11 or More Carbons In the process of producing valuable aromatics, the same feed and reaction conditions were applied, with the exception that the hydrocarbonaceous components having 11 or more carbons resulting from hydroprocessing and hydrocracking were recirculated back to the hydrogenation and reaction area.

The coal tar feed (A0), the product (A1) obtained without recirculating hydrocarbons having 11 or more carbons, and the product (A2) obtained by recirculating hydrocarbons having 11 or more carbons are shown in Table 14 below.

TABLE 14

| Composition | A0 | A1 | A2 |
|---|---|---|---|
| Paraffin | 0.77 | 40.82 | 53.21 |
| Ethane | 0.00 | 3.07 | 4.03 |
| Propane | 0.77 | 11.43 | 14.74 |
| Butane | 0.00 | 15.06 | 19.76 |
| Naphthene | 0.00 | 0.01 | 0.01 |
| Total of Aromatics | 99.23 | 66.77 | 57.48 |
| Total of 1-ring Aromatics | 9.73 | 46.46 | 57.48 |
| 1-ring Aromatic without naphthenic ring | 6.30 | 44.82 | 57.48 |
| B | 2.05 | 28.20 | 36.99 |
| T | 0.70 | 0.00 | 0.00 |
| X | 1.59 | 15.01 | 19.69 |
| C9 | 1.65 | 0.00 | 0.00 |
| C10 | 0.30 | 1.33 | 0.79 |
| 1-ring Aromatic with one naphthenic ring | 3.43 | 1.64 | 0.00 |
| 1-ring Aromatic with two naphthenic rings | 0.00 | 0.00 | 0.00 |
| Total of 2-ring Aromatics | 89.50 | 20.29 | 0.00 |
| 2-ring Aromatic without naphthenic ring | 66.92 | 20.27 | 0.00 |
| 2-ring Aromatic with one naphthenic ring | 22.58 | 0.02 | 0.00 |
| 2-ring Aromatic with two naphthenic rings | 0.00 | 0.00 | 0.00 |
| Total of 3-ring Aromatics | 0.00 | 0.02 | 0.00 |
| Others | 0.00 | 0.56 | 0.00 |

As is apparent from Table 14, recirculation was additionally performed, whereby the aromatic components having two or more rings were excluded and as the valuable aromatic components, benzene was increased by 31% and xylene was further increased by 31%. Also, the total of light paraffins was increased by about 30%. Therefore, higher yields of the valuable aromatics and light paraffins could be obtained because of recirculation.

Production of Valuable Aromatics and Light Paraffins from Coal Tar by Recirculation of Unconverted Oils after Transalkylation In the process of producing valuable aromatics by recirculating the hydrocarbonaceous components having 11 or more carbons to the hydroprocessing unit, the same feed and reaction conditions were applied, with the exception that among valuable aromatic components resulting from transalkylation, a portion of the benzene, toluene and xylene was recovered via the aromatic separation process, and the remainder thereof was repetitively recirculated back to the transalkylation process and the hydrogenation and reaction area.

The coal tar feed (A0), the product (A1) obtained without recirculating hydrocarbons having 11 or more carbons, the product (A2) obtained by recirculating hydrocarbons having 11 or more carbons, and the product (A3) obtained by recirculating unconverted heavy oils after transalkylation are shown in Table 15 below.

TABLE 15

| Composition | A0 | A1 | A2 | A3 |
|---|---|---|---|---|
| Paraffin | 0.77 | 40.82 | 53.21 | 53.66 |
| Ethane | 0.00 | 3.07 | 4.03 | 4.07 |
| Propane | 0.77 | 11.43 | 14.74 | 14.78 |
| Butane | 0.00 | 15.06 | 19.76 | 19.80 |
| Naphthene | 0.00 | 0.01 | 0.01 | 0.01 |
| Total of Aromatics | 99.23 | 66.77 | 57.48 | 57.02 |
| Total of 1-ring Aromatics | 9.73 | 46.46 | 57.48 | 57.02 |
| 1-ring Aromatic without naphthenic ring | 6.30 | 44.82 | 57.48 | 57.02 |
| B | 2.05 | 28.20 | 36.99 | 37.07 |
| T | 0.70 | 0.00 | 0.00 | 0.00 |
| X | 1.59 | 15.01 | 19.69 | 19.96 |
| C9 | 1.65 | 0.00 | 0.00 | 0.00 |
| C10 | 0.30 | 1.33 | 0.79 | 0.00 |
| 1-ring Aromatic with one naphthenic ring | 3.43 | 1.64 | 0.00 | 0.00 |
| 1-ring Aromatic with two naphthenic rings | 0.00 | 0.00 | 0.00 | 0.00 |
| Total of 2-ring Aromatics | 89.50 | 20.29 | 0.00 | 0.00 |
| 2-ring Aromatic without naphthenic ring | 66.92 | 20.27 | 0.00 | 0.00 |
| 2-ring Aromatic with one naphthenic ring | 22.58 | 0.02 | 0.00 | 0.00 |
| 2-ring Aromatic with two naphthenic rings | 0.00 | 0.00 | 0.00 | 0.00 |
| Total of 3-ring Aromatics | 0.00 | 0.02 | 0.00 | 0.00 |
| Others | 0.00 | 0.56 | 0.00 | 0.00 |

As is apparent from Table 15, recirculation was carried out two times, whereby the amount of benzene and xylene which are valuable aromatic components was increased by 0.3 wt %, and the amount of light paraffins such as ethane, propane and butane was increased by 0.12 w %, compared to the product (A2) when recirculation was performed one time. Therefore, higher yields of the valuable aromatics could be obtained by carrying out recirculation two times.

Production of Valuable Aromatics and Light Paraffins from Coal Tar by Xylene Process after Transalkylation In the recirculation of unconverted oils after transalkylation, the same feed and reaction conditions were applied, with the exception that the xylene mixture obtained by transalkylation were treated with xylene process comprising para-xylene separation and xylene isomerization.

The coal tar feed (A0), the product (A1) obtained without recirculating hydrocarbons having 11 or more carbons, the product (A2) obtained by recirculating hydrocarbons having 11 or more carbons, the product (A3) obtained by recirculating unconverted heavy oils after transalkylation, and the product (A4) obtained by xylene isomerization and separation are shown in Table 16 below.

TABLE 16

| Composition | A0 | A1 | A2 | A3 | A4 |
|---|---|---|---|---|---|
| Paraffin | 0.77 | 40.82 | 53.21 | 53.66 | 54.30 |
| Ethane | 0.00 | 3.07 | 4.03 | 4.07 | 4.59 |
| Propane | 0.77 | 11.43 | 14.74 | 14.78 | 14.84 |
| Butane | 0.00 | 15.06 | 19.76 | 19.80 | 19.80 |
| Naphthene | 0.00 | 0.01 | 0.01 | 0.01 | 0.01 |
| Total of Aromatics | 99.23 | 66.77 | 57.48 | 57.02 | 56.42 |
| Total of 1-ring Aromatics | 9.73 | 46.46 | 57.48 | 57.02 | 56.42 |
| 1-ring Aromatic without naphthenic ring | 6.30 | 44.82 | 57.48 | 57.02 | 56.42 |
| B | 2.05 | 28.20 | 36.99 | 37.07 | 38.42 |
| T | 0.70 | 0.00 | 0.00 | 0.00 | 0.00 |
| Mixed-X | 0.97 | 13.64 | 19.69 | 18.11 | 18.00(*) |
| EB | 0.63 | 1.38 | 1.81 | 1.85 | 0.00 |
| C9 | 1.65 | 0.00 | 0.00 | 0.00 | 0.00 |
| C10 | 0.30 | 1.33 | 0.79 | 0.00 | 0.00 |
| 1-ring Aromatic with one naphthenic ring | 3.43 | 1.64 | 0.00 | 0.00 | 0.00 |
| 1-ring Aromatic with two naphthenic rings | 0.00 | 0.00 | 0.00 | 0.00 | 0.00 |
| Total of 2-ring Aromatics | 89.50 | 20.29 | 0.00 | 0.00 | 0.00 |
| 2-ring Aromatic without naphthenic ring | 66.92 | 20.27 | 0.00 | 0.00 | 0.00 |
| 2-ring Aromatic with one naphthenic ring | 22.58 | 0.02 | 0.00 | 0.00 | 0.00 |
| 2-ring Aromatic with two naphthenic rings | 0.00 | 0.00 | 0.00 | 0.00 | 0.00 |
| Total of 3-ring Aromatics | 0.00 | 0.02 | 0.00 | 0.00 | 0.00 |
| Others | 0.00 | 0.56 | 0.00 | 0.00 | 0.00 |

(*)Para-Xylene

As is apparent from Table 16, almost all of the xylene mixture could be converted into para-xylene which is a valuable product by para-xylene separation and xylene isomerization, and ethylbenzene (EB) which is an impurity in the xylene component was completely removed and converted into benzene. Therefore, the yield and purity of valuable aromatics could be increased by additionally carrying out xylene process.

Although the embodiments of the present invention have been disclosed for illustrative purposes, those skilled in the art will appreciate that a variety of different modifications and substitutions are possible, without departing from the scope and spirit of the invention as disclosed in the accompanying claims. Accordingly, such modifications and substitutions should also be understood as falling within the scope of the present invention.

The invention claimed is:

1. A method of producing aromatics and light paraffins, comprising:
a) introducing oils derived from oil, coal or wood into a hydrogenation and reaction area comprising a hydroprocessing process and a hydrocracking process;
b) hydroprocessing the oils in the presence of a hydroprocessing catalyst to partially saturate aromatic components having two or more aromatic rings into aromatic components having one aromatic ring, such that an amount of aromatic components having one aromatic ring in the oils is increased;
c) hydrocracking the hydroprocessed oils in the presence of a hydrocracking catalyst to form hydrocracked oils;
d) separating the hydrocracked oils into
i. hydrocarbonaceous components having 11 or more carbons,
ii. hydrocarbonaceous components having 6-10 carbons, and
iii. hydrocarbonaceous components having 5 or fewer carbons; and
e) recirculating the hydrocarbonaceous components having 11 or more carbons to the hydrogenation and reaction area;
f) feeding the hydrocarbonaceous components having 6-10 carbons to an aromatic separation process or a transalkylation process,
wherein:
hydrocarbonaceous components having 6-10 carbons fed to the aromatic separation are separated into a first portion and a second portion,
the first portion is fed to a transalkylation process and contacted with a transalkylation catalyst to form a transalkylated product comprising benzene, toluene, xylenes and hydrocarbonaceous components having 9 or more carbons,
the transalkylated product is mixed with the second portion in the aromatic separation process, and
hydrocarbonaceous components having 11 or more carbons, hydrocarbonaceous components having 6-10 carbons, a xylene mixture comprising ortho-xylene, meta-xylene, and para-xylene, and/or an aromatics stream comprising benzene, toluene, xylenes or mixtures thereof, are separated in the aromatic separation process; or
hydrocarbonaceous components having 6-10 carbons fed to the transalkylation process are contacted with a transalkylation catalyst to form a transalkylated product comprising benzene, toluene, xylenes and hydrocarbonaceous components having 9 or more carbons
the transalkylated product is fed to an aromatic separation process, and
hydrocarbonaceous components having 11 or more carbons, hydrocarbonaceous components having 6-10 carbons, a xylene mixture comprising ortho-xylene, meta-xylene, and para-xylene, and/or an aromatics stream comprising benzene, toluene, xylenes or mixtures thereof, are separated in the aromatic separation process; and
g) feeding the hydrocarbonaceous components having 5 or fewer carbons to a light separation process to recover paraffins;
wherein the oils derived from oil contain 15-99 wt % aromatic components based on total hydrocarbonaceous components and have a boiling point of 70-700° C.; and
wherein the oils derived from coal or wood contain 40-99 wt % aromatic components based on total hydrocarbonaceous components and have a boiling point of 70-700° C.

2. The method of claim 1, further comprising (h) feeding the xylene mixture separated in the aromatic separation process to a xylene process, separating para-xylene from the xylene mixture, isomerizing meta- and ortho-xylenes into para-xylene, and recirculating isomerized product other than para-xylene to the aromatic separation process.

3. The method of claim 1, wherein the hydroprocessing catalyst comprises an alumina carrier and one or more metals selected from the group consisting of of Groups 6, 9 and 10 metals supported thereon.

4. The method of claim 1, wherein the hydrocracking catalyst is a modified zeolite catalyst having one or more metals selected from the group consisting of Mo, W, Co and Ni supported thereon.

5. The method of claim 4, wherein the modified zeolite catalyst comprises one or more zeolites having a pore size of 4 Å or more, and is modified with a binder.

6. The method of claim 5, wherein the modified zeolite catalyst comprises one or more zeolites selected form the group consisting of MOR, MEL, FAU, and BEA.

7. The method of claim 1, wherein the oils derived from oil, coal or wood are selected from raw pyrolysis gasoline (RPG), heavy raw pyrolysis gasoline (heavy RPG), treated pyrolysis gasoline (TPG), reformate, heavy aromatics, kerosene, jet oil, atmospheric gas oil, FCC (fluid catalytic cracking) gasoline, light cracked naphtha, heavy cracked naphtha, FCC decanted oil, vacuum gas oil, coker gas oil, coker diesel, coker naphtha, heavy and reduced petroleum crude oil, petroleum atmospheric distillation bottom, petroleum vacuum distillation bottoms, asphalt, bitumen, tar sand oil, shale oil, coal tar, tar oil, light oil, phenolic oil or carbolic oil, naphthalene oil, wash oil, anthracene oil, light anthracene oil, heavy anthracene oil, pitch, wood tar, hardwood tar, resinous tar, and mixtures thereof.

8. The method of claim 2, further comprising recirculating the hydrocarbonaceous components having 11 or more carbons obtained from the aromatic separation process to the hydrogenation and reaction area and feeding the hydrocarbonaceous components having 6-10 carbons obtained from the aromatic separation process to the transalkylation process.

9. The method of claim 1, further comprising (d') separating saturated hydrocarbons including cyclohexane from the (ii) hydrocarbonaceous components having 6-10 carbons prior to step (f), feeding the saturated hydrocarbonaceous components to a reformer to form unsaturated hydrocarbon components, and feeding the unsaturated hydrocarbon components to step (f).

10. The method of claim 9, wherein the reformer is operated at a temperature of 400-600° C. in a hydrogen atmosphere using a $Pt/Al_2O_3$, $Pt$—$Re/Al_2O_3$ or $Pt$—$Sn/Al_2O_3$ catalyst.

11. The method of claim 1, wherein the transalkylation catalyst comprises:
a carrier composed of 10-95 wt % of beta-zeolite or mordenite having a molar ratio of silica/alumina adjusted to 20-200 based on alumina and 5-90 wt % of one or more inorganic binders selected from the group consisting of gamma-alumina, silica, silica alumina, bentonite, kaolin, clinoptilolite and montmorillonite; and
a hydrogenation metal composed of, based on 100 parts by weight of the carrier, 0.001-0.5 parts by weight of one or more metals selected form the group consisting of platinum, tin, indium and lead.

12. A method of producing aromatics and light paraffins, comprising:
a) introducing oils derived from oil, coal or wood into a hydrogenation and reaction area comprising a hydrocracking process and a hydroprocessing process;
b) hydrocracking the oils in the presence of a hydrocracking catalyst to form hydrocracked oils;
c) hydroprocessing the hydrocracked oils in the presence of a hydroprocessing catalyst to partially saturate aromatic components having two or more aromatic rings into aromatic components having one aromatic ring, such that an amount of aromatic components having one aromatic ring in the hydrocracked oils is increased, and to form hydroprocessed oils;
d) separating the hydroprocessed oils into
  i. hydrocarbonaceous components having 11 or more carbons,
  ii. hydrocarbonaceous components having 6-10 carbons, and
  iii. hydrocarbonaceous components having 5 or fewer carbons; and
e) recirculating the hydrocarbonaceous components having 11 or more carbons to the hydrogenation and reaction area;
f) feeding the hydrocarbonaceous components having 6-10 carbons to an aromatic separation process or a transalkylation process,
  wherein:
    hydrocarbonaceous components having 6-10 carbons fed to the aromatic separation are separated into a first portion and a second portion,
    the first portion is fed to a transalkylation process and contacted with a transalkylation catalyst to form a transalkylated product comprising benzene, toluene, xylenes and hydrocarbonaceous components having 9 or more carbons,
    the transalkylated product is mixed with the second portion in the aromatic separation process, and
    hydrocarbonaceous components having 11 or more carbons, hydrocarbonaceous components having 6-10 carbons, a xylene mixture comprising ortho-xylene, meta-xylene, and para-xylene, and/or an aromatics stream comprising benzene, toluene, xylenes or mixtures thereof, are separated in the aromatic separation process; or
    hydrocarbonaceous components having 6-10 carbons fed to the transalkylation process are contacted with a transalkylation catalyst to form a transalkylated product comprising benzene, toluene, xylenes and hydrocarbonaceous components having 9 or more carbons
    the transalkylated product is fed to an aromatic separation process, and
    hydrocarbonaceous components having 11 or more carbons, hydrocarbonaceous components having 6-10 carbons, a xylene mixture comprising ortho-xylene, meta-xylene, and para-xylene, and/or an aromatics stream comprising benzene, toluene, xylenes or mixtures thereof, are separated in the aromatic separation process; and
g) feeding the hydrocarbonaceous components having 5 or fewer carbons to a light separation process to recover paraffins;
  wherein the oils derived from oil contain 15-99 wt % aromatic components based on total hydrocarbonaceous components and have a boiling point of 70-700° C.; and
  wherein the oils derived from coal or wood contain 40-99 wt % aromatic components based on total hydrocarbonaceous components and have a boiling point of 70-700° C.

13. The method of claim 12, further comprising (h) feeding the xylene mixture separated in the aromatic separation process to a xylene process, separating para-xylene from the xylene mixture, isomerizing meta- and ortho-xylenes into para-xylene, and recirculating isomerized product other than para-xylene to the aromatic separation process.

14. The method of claim 12, wherein the hydroprocessing catalyst comprises an alumina carrier and one or more metals selected from the group consisting of Groups 6, 9 and 10 metals supported thereon.

15. The method of claim 12, wherein the hydrocracking catalyst is a modified zeolite catalyst having one or more metals selected from the group consisting of Mo, W, Co and Ni supported thereon.

16. The method of claim 15, wherein the modified zeolite catalyst comprises one or more zeolites having a pore size of 4 Å or more, and is modified with a binder.

17. The method of claim 16, wherein the modified zeolite catalyst comprises one or more zeolites selected form the group consisting of MOR, MEL, FAU, and BEA.

18. The method of claim 12, wherein the oils derived from oil, coal or wood are selected from raw pyrolysis gasoline (RPG), heavy raw pyrolysis gasoline (heavy RPG), treated pyrolysis gasoline (TPG), reformate, heavy aromatics, kerosene, jet oil, atmospheric gas oil, FCC (fluid catalytic cracking) gasoline, light cracked naphtha, heavy cracked naphtha, FCC decanted oil, vacuum gas oil, coker gas oil, coker diesel, coker naphtha, heavy and reduced petroleum crude oil, petroleum atmospheric distillation bottom, petroleum vacuum distillation bottoms, asphalt, bitumen, tar sand oil, shale oil, coal tar, tar oil, light oil, phenolic oil or carbolic oil, naphthalene oil, wash oil, anthracene oil, light anthracene oil, heavy anthracene oil, pitch, wood tar, hardwood tar, resinous tar, and mixtures thereof.

19. The method of claim 13, further comprising recirculating the hydrocarbonaceous components having 11 or more carbons obtained from the aromatic separation process to the hydrogenation and reaction area and feeding the hydrocarbonaceous components having 6-10 carbons obtained from the aromatic separation process to the transalkylation process.

20. The method of claim 12, further comprising (d') separating saturated hydrocarbons including cyclohexane from the (ii) hydrocarbonaceous components having 6-10 carbons prior to step (f), feeding the saturated hydrocarbonaceous components to a reformer to form unsaturated hydrocarbon components, and feeding the unsaturated hydrocarbon components to step (f).

21. The method of claim 20, wherein the reformer is operated at a temperature of 400-600° C. in a hydrogen atmosphere using a $Pt/Al_2O_3$, $Pt-Re/Al_2O_3$ or $Pt-Sn/Al_2O_3$ catalyst.

22. The method of claim 12, wherein the transalkylation catalyst comprises:
a carrier composed of 10-95 wt % of beta-zeolite or mordenite having a molar ratio of silica/alumina adjusted to 20-200 based on alumina and 5-90 wt % of one or more inorganic binders selected from the group consisting of gamma-alumina, silica, silica alumina, bentonite, kaolin, clinoptilolite and montmorillonite; and
a hydrogenation metal composed of, based on 100 parts by weight of the carrier, 0.001-0.5 parts by weight of one or more metals selected form the group consisting of platinum, tin, indium and lead.

* * * * *